United States Patent [19]
McKay

[11] Patent Number: 5,474,543
[45] Date of Patent: Dec. 12, 1995

[54] SINGLE NEEDLE APPARATUS AND METHOD FOR PERFORMING RETROPUBIC URETHROPEXY

[76] Inventor: Hunter A. McKay, 18 Meadow La., Mercer Island, Wash. 98040

[21] Appl. No.: 62,136

[22] Filed: May 17, 1993

[51] Int. Cl.$^6$ ............................................. A61M 5/32
[52] U.S. Cl. ..................... 604/272; 606/144; 606/232
[58] Field of Search ..................... 128/898; 604/264, 604/272; 606/119, 144–151, 232, 233, 207; 600/29, 30, 31

[56] References Cited

U.S. PATENT DOCUMENTS

| | | | |
|---|---|---|---|
| 659,422 | 10/1900 | Shidler | 606/144 |
| 2,264,679 | 12/1941 | Ravel | 606/144 |
| 2,737,954 | 3/1956 | Knapp | 606/146 |
| 2,738,790 | 3/1956 | Todt, Sr. et al. | 604/145 |
| 2,740,404 | 4/1956 | Kohl | 606/167 |
| 4,172,458 | 10/1979 | Pereyra | 606/144 |
| 4,493,323 | 1/1985 | Albright et al. | 606/144 |
| 4,911,164 | 3/1990 | Roth | 606/148 |
| 5,041,129 | 8/1991 | Hayhurst et al. | 606/232 |
| 5,149,329 | 9/1992 | Richardson | 604/272 |
| 5,234,438 | 8/1993 | Semrad | 606/108 |
| 5,368,599 | 11/1994 | Hirsch et al. | 606/139 |
| 5,368,601 | 11/1994 | Sauer et al. | 606/144 |

*Primary Examiner*—C. Fred Rosenbaum
*Assistant Examiner*—V. Alexander

[57] ABSTRACT

A suturing needle asssembly used for the retropubic surgical correction of anatomical stress incontinence due to pelvic relaxation, the suturing needle assembly having an array of four needles inside a protective sheath. The sheath protects fragile tissues from inadvertent penetration by the four needles, each of which has an eyelet for capture of a surgical suture. The spacing of the four needles within the sheath allows for the precise positioning of two sutures (previously woven through a polypropylene "bolster") underneath the endopelvic fascia at the junction of the bladder neck and urethra. According to a method of the present invention, the suturing needle assembly is positioned retropubically at the right side of the bladder neck and the needle points extruded from within the sheath, thus penetrating through the endopelvic fascia. Through a small vaginotomy, a previously fashioned flat bolster is positioned beneath the endopelvic fascia and the four needle points used to capture the two monofilament sutures passing through the bolster. Cephalad withdrawal of the instrument positions the four suture ends into the retropubic region for securing to Cooper's ligament. An identical procedure is done on the left side. As a result, anterior pelvic relaxation and stress urinary incontinence are corrected with a high degree of success.

16 Claims, 5 Drawing Sheets

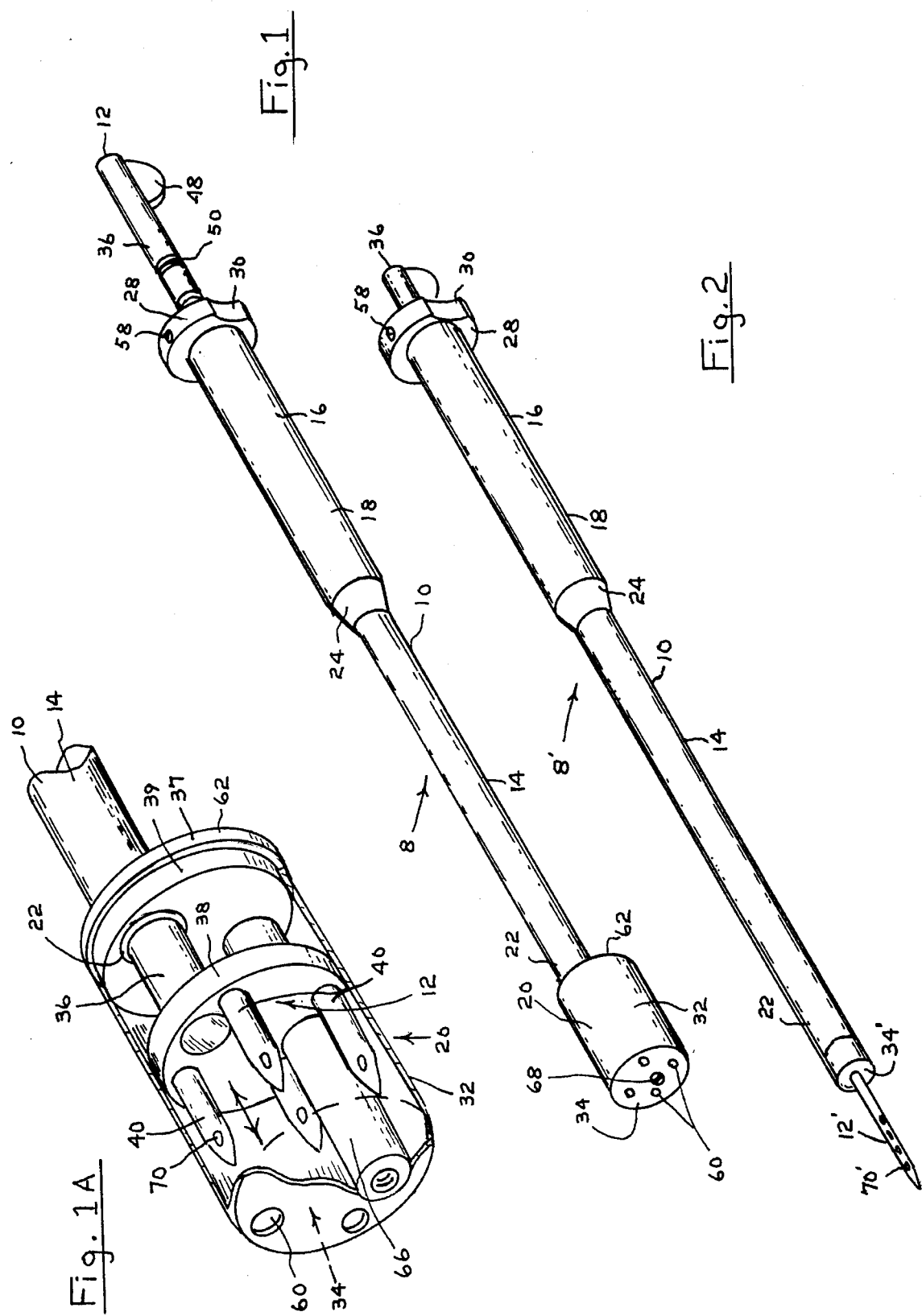

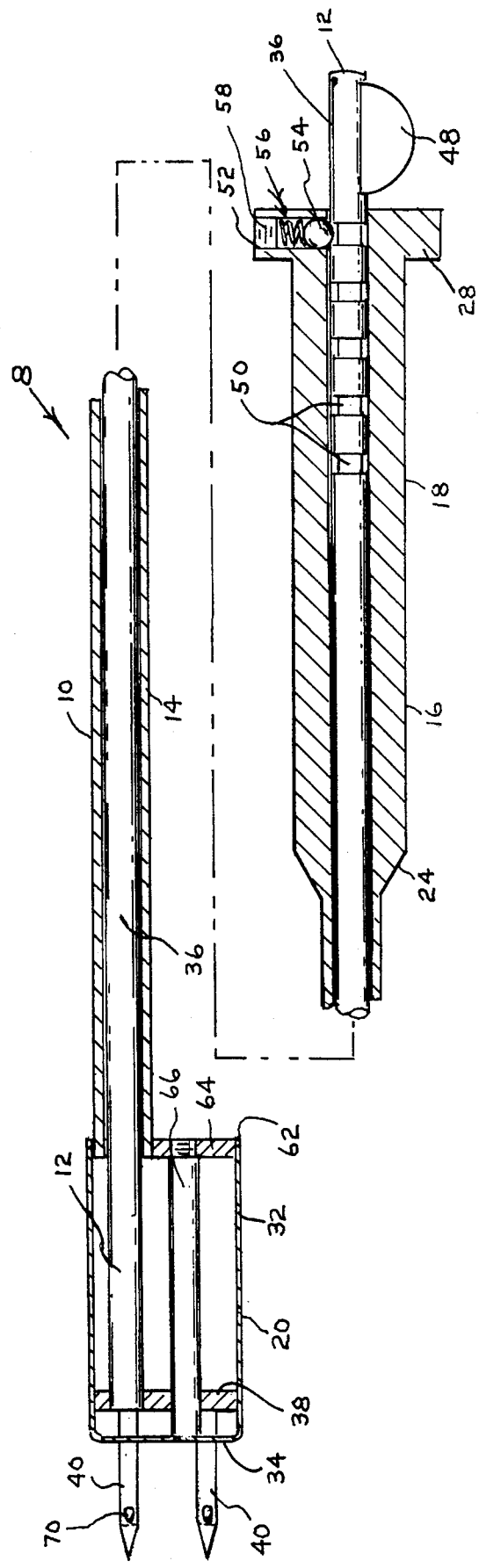
Fig. 3
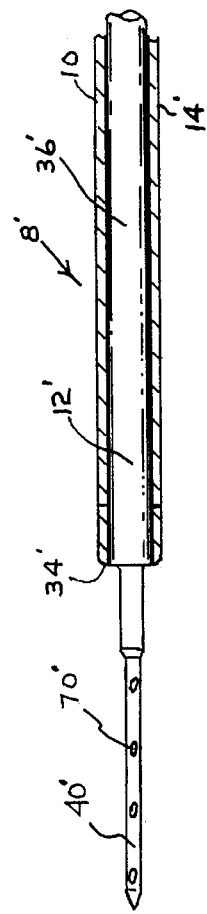
Fig. 4
Fig. 10

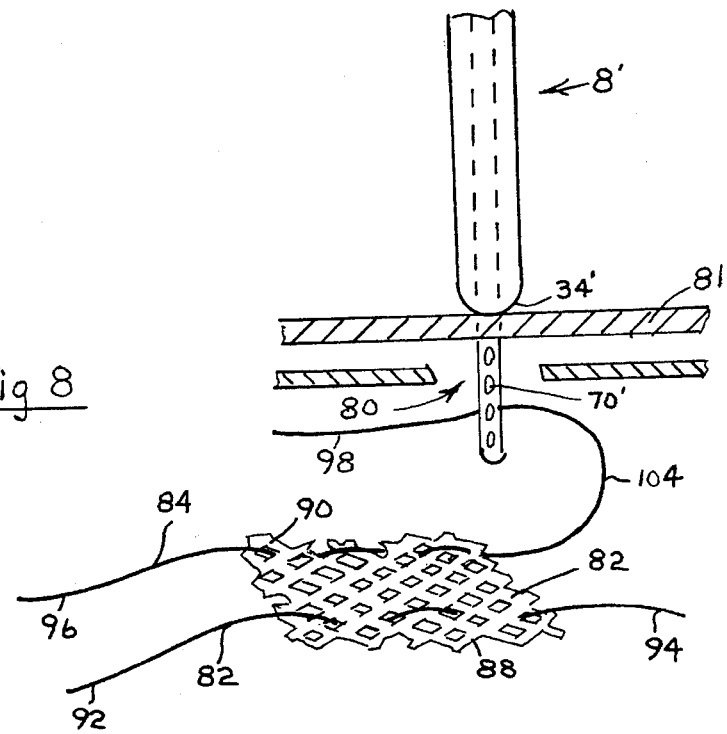
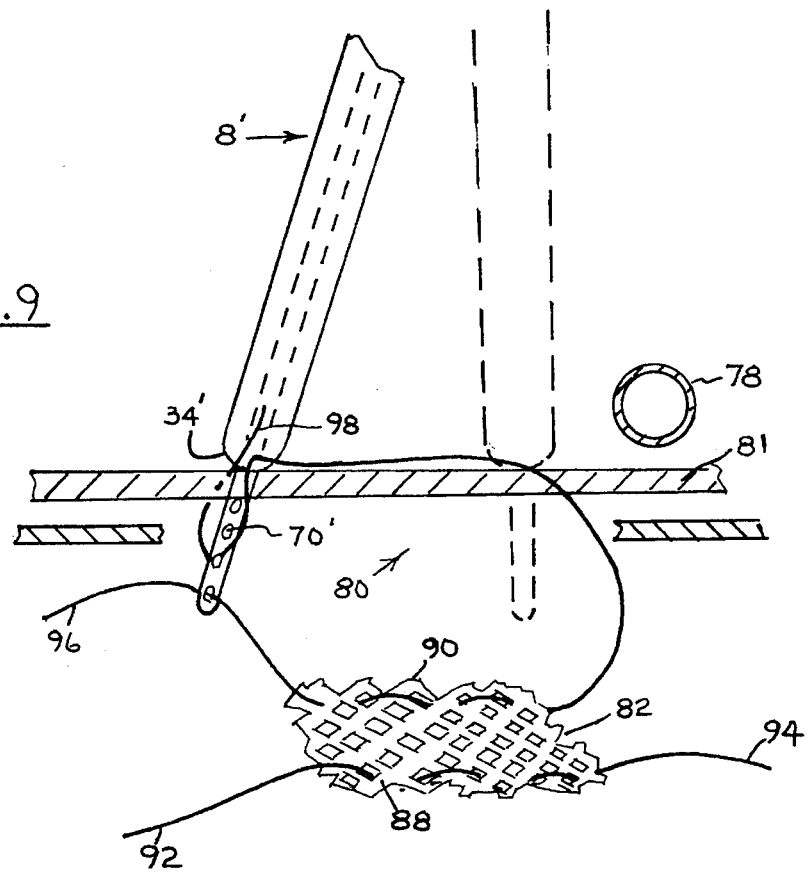

SINGLE NEEDLE APPARATUS AND METHOD FOR PERFORMING RETROPUBLIC URETHROPEXY

BACKGROUND OF THE INVENTION

1. Field of the Invention

The invention relates generally to an apparatus and method for performing a retropubic urethropexy procedure to correct female stress incontinence, and more specifically to a single needle assembly apparatus and method for manipulating a plurality of sutures, preferably suspending a surgical bolster, to facilitate the surgical procedure and improve morbidity.

2. Description of the Prior Art

Relaxation of muscles and tissues supporting the bladder neck can produce stress incontinence in the human female. Surgical correction of this condition can be effective when the bladder neck can be elevated and supported from above with heavy, non-absorbable sutures. Surgical procedures for this purpose have evolved from purely retropubic operations such as the Marshall-Marchetti procedure described in journal article "The Correction of Stress Incontinence by Simple Vesicourethral Suspension", Marshall, V. F., Marchetti, A. A., Krantz, K. E., Surgery Gynecology and Obstetrics, 88:590, 1949, and its variants such as described in the journal article "Urethrovaginal Fixation to Cooper's Ligament for Correction of Stress Incontinence, Cystocele, and Prolapse:, Burch, J. C., American Journal of Obstetrics and Gynecology, 81:281, 1961, to combined retropubic and vaginal operations. Such procedures are, for example, described in journal articles: "Combined Urethrovesical Suspension and Vaginourethroplasty for Correction of Urinary Stress Incontinence", Peyrera, A. J., and Lebherz, T. B., Obstetrics and Gynecology, 30:537, 1967; "Endoscopic Suspension of the Vesical Neck for Urinary Incontinence", Stamey, T. A., Surgery Gynecology and Obstetrics, 136:547, 1973; and "Modified Bladder Neck Suspension for Female Stress Incontinence", Raz, S., Suspension for Female Stress Incontinence", Raz, S., Urology, 17:82, 1981. This group of surgical operations, commonly and collectively referred to as needle suspensions, requires precise positioning of various needles for the placement of the heavy, non-absorbable sutures. Endoscopic confirmation of needle and suture placement has proven a valuable aspect of these operations.

However, technical difficulties with placement of the various needles in patients who have undergone prior incontinence surgery may result in repeated entries into the bladder, and/or less than optimal positioning of the sutures at other than the precise bladder neck. The relatively small cross-section of the sutures can produce physical stresses on the supported tissues that eventually cause the sutures to bear into the supported tissues, reversing the effect of the surgery.

SUMMARY OF THE INVENTION

Broadly, the invention is a single needle assembly apparatus to use in performing a retropubic urethropexy. The apparatus includes a needle sheath having a blunt end and a single suture needle assembly including at least one suture needle slideably carried within the sheath for reciprocal movement between a first position with the suture needle fully received within the sheath and a second position in which each suture needle point is extended longitudinally outwardly from the blunt end of the sheath. The suture needle assembly further includes means for engaging and drawing a plurality of sutures.

In one embodiment of the apparatus, the suture needle assembly includes a plurality of needles, each provided with a single eye, and fixedly secured to a single needle actuator. In another embodiment of the invention, the single needle assembly includes a single needle point provided with a plurality of longitudinally spaced eyes. The apparatus is sequentially positioned at the optimal placement locations of the sutures and the needle extended to pierce the tissue to be supported. Sutures are engaged with the eyes and drawn through the tissue and subsequently secured to appropriate supporting structure as described in more detail below.

In a preferred embodiment of the invention, there is provided a surgical bolster having a pair of supporting sutures woven into its opposite edges, the sutures extending outwardly from the corners of the bolster. When the sutures are drawn through the supporting tissue and secured, the bolster substantially increases the area of supported tissue.

The method of the invention includes the steps of placing the needle sheath with the needle assembly retracted therein to precisely position the needle, and then extending the needle assembly to pierce the supporting tissue with the needles. The sutures are engaged and drawn back through the tissue and secured. The piercing step includes either a single maneuver using a multiple needle assembly or a sequential maneuver using a single needle assembly with multiple eyes.

Another objective of the invention is to provided an apparatus which facilitates accurate placement of supporting sutures placed in a retropubic urethropexy.

Still another objective of the invention is to provide a single needle assembly apparatus which simplifies the placement of sutures in such an operation.

Yet another objective of the invention is to provide a single needle assembly for use in performing a retropubic urethropexy which includes a surgical bolster having supporting sutures woven into opposite edges and extending outwardly from the bolster corners for engagement with the multiple eyes of the needle assembly.

Another objective of the invention is to provide an improved method for performing a retropubic urethropexy which increases accuracy of placement of supporting sutures, simplifies suture placement, and improves morbidity of the operation.

BRIEF DESCRIPTION OF THE DRAWINGS

These and other objectives of the invention and the invention itself will be better understood in view of the following detailed description taken in conjunction with the attached drawings wherein like numerals denote like elements and wherein:

FIG. 1 is an isometric illustration of one embodiment of the apparatus of the invention showing details of the single needle assembly using multiple needles;

FIG. 1A is a fragmentary cutaway illustration showing details of the single needle assembly in FIG. 1;

FIG. 2 is an isometric illustration of the single needle assembly apparatus incorporating a single needle;

FIGS. 3 and 4 are axial sectional views of the embodiments of FIGS. 1 and 2, respectively;

FIGS. 8 and 9 are diagramatic illustrations showing application of the single needle embodiment of the apparatus in the method of the invention; and, FIG. 10 is a fragmentary axial view of an alternative suture engaging means.

DETAILED DESCRIPTION

Figure 5:
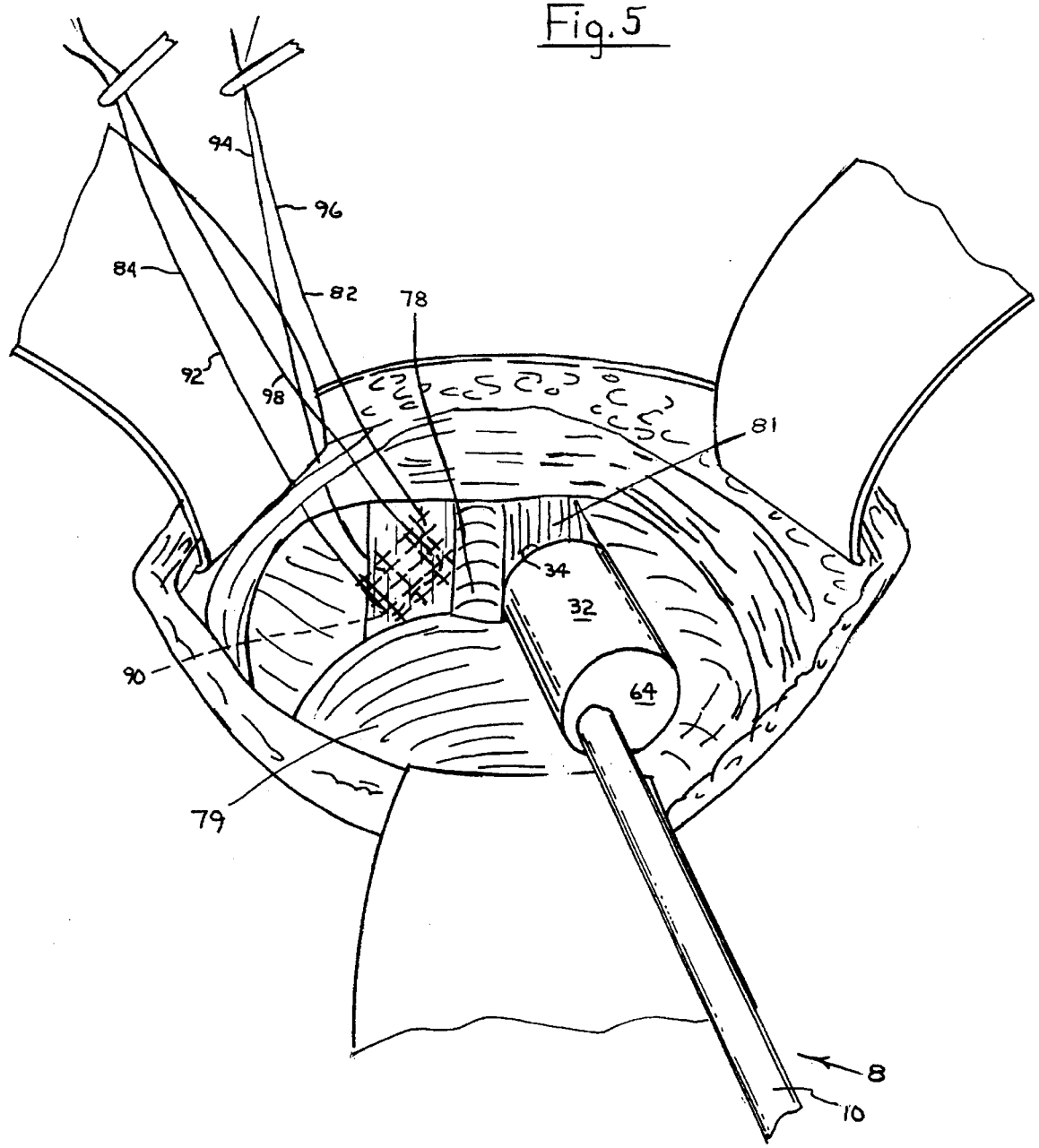
FIGS. 5 through 7 are a sequence of illustrations showing application of the multiple needle embodiment in the method of the invention.
Figure 6:
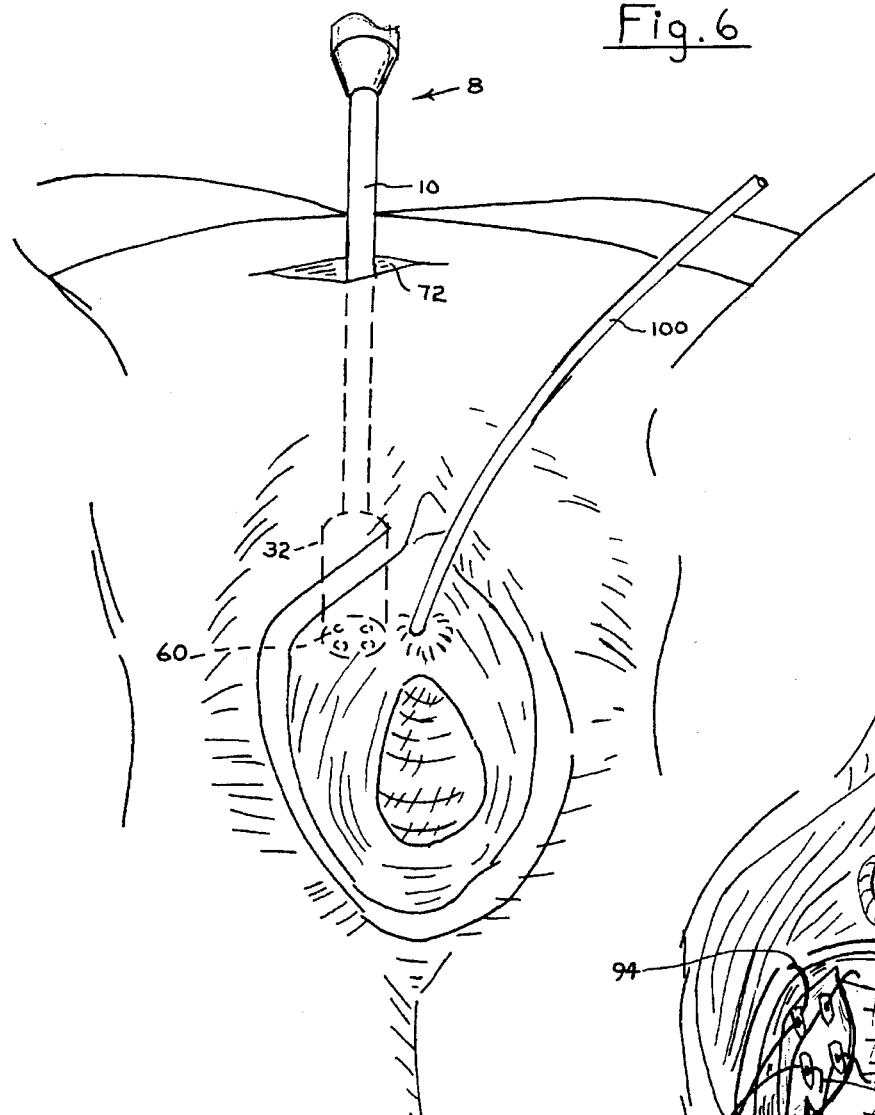
Figure 7:
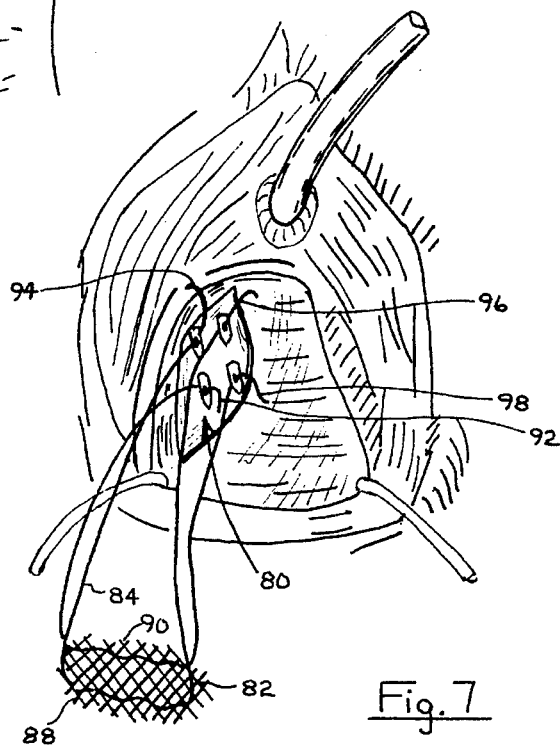

Referring now to the drawings, a single needle assembly surgical apparatus in accordance with the invention is shown generally at 8 in FIGS. 1, 1A, and 3. The apparatus comprises a sheath 10 and a single needle assembly 12 slideably received therein.

The sheath 10 includes an elongated, thin walled tubular member 14 having a handgrip 16 at one end 18, and a needle housing 20 at its opposite end 22. The handgrip 16 is a hollow cylindrical member having a tapered end surface 24 disposed toward the member 14. The end 18 of the handgrip is provided with an enlarged diameter flange 28 having a thumb engaging arcuate recess 30 formed in one side thereof. The arcuate recess enables accurate rotational positioning of the apparatus. The handgrip 56 may be formed of a single piece with the sheath.

The needle housing 20 includes a hollow cylindrical end cap 32 having a blunt end 34, and an annular member 64. Member 64 is fixedly secured to the sheath 10 with its axis parallel to and offset from the axis of the sheath. The perimetral edge of member 64 is provided with a rabbet 39 which positively engages the inner surface of the cap 32.

A guide shaft is fixedly mounted to member 64 in parallel spaced relationship to the axis of the sheath. The end cap is secured to the distal end of the shaft by means such as screw 68.

The single needle assembly includes an elongated operator 36 and a needle supporting disk 38 fixedly secured thereto. A plurality of needles 40, there being four such points 40 in the preferred embodiment of the invention, are fixedly secured to the disk 38 in parallel relationship to the axis of the sheath. The operator 36 has an external diameter dimensioned to slide smoothly within the sheath and a length such that its end extends outwardly from the end of sheath opposite the needle housing 20. End 46 is provided with an arcuate tab portion 48, and a plurality of axially spaced annular slots as at 50. Flange 28 is provided with a radially extending threaded hole 52 in which are received a detent ball 54 engageable with individual ones of the slots 50, and a coil spring 56 compressed against ball 54 by a set screw 58.

The needle point supporting disk 38 has a diameter dimensioned to slide smoothly within end cap 32. In a working embodiment of the invention, the needles are spaced about 13 mm apart, and each is provided with a suture receiving eye 70, the cap 34 having an array of apertures 60 therethrough in registry with and slideably receiving respective ones of the needles.

Each needle point 40 is provided with a suture engaging eye 70. Alternately, the needle points may be provided with a suture engaging annular slot 70", FIG. 10 only In an alternative embodiment of the invention shown in FIGS. 2 and 4, the single needle assembly is provided with a single needle 40'. The single needle is provided with four axially spaced eyes 70'. The needle is formed as a single piece with operator 36'. The needle supporting disk is not used. It will be appreciated that individual ones of the eyes 70' will be sequentially exposed as the operator is incrementally extended. Proper spacing of the annular groves 50 will provide a positive and tactile incremental movement.

In operation, the operator is moveable from a first position to the right (as viewed in the drawings) to a second extended position to the left (again as viewed in the drawings). The operator can be moved in easily metered increments due to the action of the detent mechanism. When the operator is in its first position, the needles are fully withdrawn into the sheath and only a blunt end is presented by the instrument. As explained in more detail below, when the instrument is positioned during an operation, the operator and single needle assembly can be extended to pierce tissue as required.

In a retropubic urethropexy operation in accordance with the invention, the patient is prepared for a combined abdominal and vaginal surgery in the low lithotomy position. A short incision at the symphysis pubis is made to provide access to the rectus fascia. The rectus fascia is opened longitudinally for about 6 cm. This allows limited entry into the space of Retzius 76 and permits blunt finger dissection alongside the urethra, 78, the bladder neck, and bladder 79, previously filled with 400 cc. of sterile water via a Malecot urethral catheter 100. Sharp dissection using heavy Mayo scissors and/or electrocautery are usually necessary if the patient has had prior retropubic surgery. Filling the bladder to capacity facilitates this procedure and prevents inadvertent entry into the bladder in most instances.

The apparatus 8, with the needles in the first (withdrawn) position, is used to bluntly push the rectus fascia and any perivaginal adhesions from previous surgeries medially. This frees the lateral periurethral space. If the space permits, the instrument of FIG. 1 is positioned precisely at the right side of the bladder neck and the four needles are extended to pierce the endopelvic fascia 81 only. Note that filling the bladder facilitates the accurate localization of the instrument. A longitudinal vaginotomy 80 is now made directly between the four needles, and the four needles are delivered into the vaginotomy without epithelial entrapment. No significant disruption of the endopelvic fascia occurs, and blood loss is minimal. The advantage of the embodiment of FIG. 1 is that the 13 mm. spacing between the needle points ensures that a good web of supporting endopelvic fascia will be available for the suspension. A previously fashioned flat surgical bolster 82 about 20×25 mm and made of a material such as Prolene or Marlex mesh has color coded number 2 black nylon and blue Novafil or Prolene sutures 84, 86, woven along the long edges 88, 90. The four suture ends 92, 94, 96, and 98 are placed through respective eyes 40 of the needles and the entire instrument is withdrawn in a cephalad maneuver. This delivers the two black and the two blue suture ends into the suprapubic area. An identical procedure is performed along the left side of the bladder neck. At this time, cystoscopic confirmation of the suture placement is desirable. It should be noted that cystoscopic confirmation can be performed at earlier phases of the procedure if necessary, particularly if there is concern about possible bladder penetration. A suprapubic tube is now placed. A physiologic test is performed using the Crede maneuver to reproduce leakage. The leakage should disappear with mild traction on the right, left, or both groups of sutures.

Failure to demonstrate this correction usually means that there are still fixating adhesions preventing full mobility of the proximal urethra, or in rare instances, that the suture placement is too lateral. Corrective measures can be taken to produce a positive test. Copious irrigation is followed with closure of the vaginotomies with 3-0 Vicryl suture.

Cooper's ligaments 101 on the patient's right and left side are now identified, cleaned, and then used for placement of the right and left suture groups, respectively. The black sutures, which are positioned along the cephalad aspect of the bolster, are passed in the more lateral position on Cooper's ligament and have moderate tension applied when tied. These are the more important of the sutures because of their position at the bladder neck. The blue sutures are passed through a more medial position on Cooper's ligament and tied with minimal tension. Wound closure is routine. Copious antibiotic irrigation (from a cystoscopic fluid bag) and parenteral antibiotics are essential.

If there is insufficient space to place the instrument of FIG. 1, usually due to severe scarring and adhesions, the smaller diameter instrument of FIG. 2 is used. The diameter of this instrument end portion is about 9 mm and can be delivered into a minimally dissected entry alongside the bladder neck. The operator is incrementally extended and the single needle 40' pierces the endopelvic fascia and enters a vaginotomy as described above and a single black suture picked up. The needle is withdrawn into the sheath which remains at all times above the endopelvic fascia. The blunt end 34' of the apparatus is next moved about 15 mm. lateral to the bladder neck and the needle again pierced through the endopelvic fascia and the second end of the black suture is picked up. The entire instrument is now withdrawn, delivering the two black suture ends. The instrument is now positioned about 10 to 15 mm. distally down the urethra and the procedure repeated as above to deliver the ends of the two blue sutures. The remainder of the operation is identical to that described above using the multiple needle embodiment.

It will now be seen that the apparatus and method of the invention provide improvement in apparatus and procedure for performing a retropubic urethropexy operation. The apparatus and method facilitate accurate placement of sutures, simplify the procedure, and, using the surgical bolster, provide a procedure having significantly improved morbidity. While the invention has been described with reference to specific structure and steps, various modifications thereof will be obvious to those skilled in the art without departing from the spirit or scope of the invention.

What I claim is:

1. A surgical apparatus for performing a retropubic urethrapexy, comprising:

an elongated needle sheath having a blunt end, a single suture assembly within said needle sheath including an array of needles in a fixed rectangular arrangement and parallel to each other, and a means on each end of said needles for engaging and drawing a suture and allowing for the capture of two sutures simultaneously, wherein said single suture assembly moves reciprocally between a first position with said needles within said needle sheath and a second position with said needles extended longitudinally outwardly from said blunt end of said needle sheath.

2. The apparatus of claim 1 wherein the needle sheath includes a tubular member and a needle cap forming a blunt end thereof, the needle cap having an array of apertures therethrough, each of said needles having a pointed end disposed within a respective one of the apertures when the single suture assembly is in the first position, and being extended outwardly therefrom when in the second position.

3. The apparatus of claim 2 wherein the single suture assembly further includes a needle supporting member fixedly securing each of said needles and a needle operating shaft coupled to the suture needle supporting member, a distal end of the needle operating shaft extending outwardly from the end of the needle sheath opposite the blunt end.

4. The apparatus of claim 3 further including detent means for detenting movement of the single suture assembly in a plurality of positions between the first and second positions.

5. The apparatus of claim 4 wherein the needle sheath further includes hand grip means at the end thereof opposite the needle cap, and the needle assembly operator shaft includes gripping means at the distal end thereof, both for facilitating manipulation of the apparatus.

6. The apparatus of claim 5 further including means for preventing rotation of the single suture assembly relative to the needle sheath.

7. The apparatus of claim 6 wherein the means for engaging and drawing a suture are eyes adjacent the pointed ends of each of the needles.

8. The apparatus of claim 6 wherein the means for engaging and drawing a suture are annular slots adjacent the pointed ends of each of the needles.

9. The apparatus of claim 1 further including a surgical bolster, attached to the apparatus by a pair of sutures woven through opposite walls of the bolster and extending from the corners of the bolster, individual ones of the suture being engaged by the means for engaging and drawing a suture.

10. The apparatus of claim 9 wherein the needle sheath includes a tubular member, and a needle guide member closing the blunt end thereof, the needle guide member having an array of apertures therethrough, each of said needles having a pointed end disposed within the sheath in registry with a respective one of the apertures when the single suture assembly is in the first position, and being extended outwardly therefrom when the assembly is in the second position.

11. The apparatus of claim 10 wherein the assembly further includes a needle supporting member fixedly securing the needles, and a needle operator shaft coupled to the suture needle supporting member, a distal end of the needle operating shaft extending axially outwardly from the end of the needle sheath opposite the blunt end.

12. The apparatus of claim 11 further including detent means for detenting movement of the single suture assembly in a plurality of positions between the first and second positions.

13. The apparatus of claim 12 wherein the needle sheath further includes handgrip means at one end thereof and the needleoperator shaft includes gripping means at a end thereof opposite the needles, both for facilitating manipulation of the apparatus.

14. The apparatus of claim 13 further including means for preventing rotation of the single suture needle assembly relative to the needle sheath.

15. The apparatus of claim 14 wherein the means for engaging and drawing a suture are eyes adjacent the pointed ends of each of the needles.

16. The apparatus of claim 15 wherein the means for engaging and drawing a suture are annular slots adjacent the pointed ends of each of the needles.

* * * * *

UNITED STATES PATENT AND TRADEMARK OFFICE
CERTIFICATE OF CORRECTION

PATENT NO. : 5,474,543

DATED : December 12, 1995

INVENTOR(S) : Hunter A. McKay

It is certified that error appears in the above-identified patent and that said Letters Patent is hereby corrected as shown below:

On the title page, and column 1, in the title, "Retropublic" should read --Retropubic--

Signed and Sealed this

Twenty-seventh Day of February, 1996

Attest:

BRUCE LEHMAN

Attesting Officer       *Commissioner of Patents and Trademarks*